United States Patent
Bulman et al.

(10) Patent No.: US 10,912,919 B2
(45) Date of Patent: Feb. 9, 2021

(54) EXPANDABLE SHEATH

(71) Applicant: Edwards Lifesciences Corporation, Irvine, CA (US)

(72) Inventors: Erik Bulman, Lake Forest, CA (US); Pu Zhou, Dove Canyon, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/875,706

(22) Filed: Jan. 19, 2018

(65) Prior Publication Data

US 2018/0207395 A1    Jul. 26, 2018

Related U.S. Application Data

(60) Provisional application No. 62/449,454, filed on Jan. 23, 2017.

(51) Int. Cl.
| | |
|---|---|
| *A61M 25/00* | (2006.01) |
| *A61F 2/24* | (2006.01) |
| *A61F 2/95* | (2013.01) |
| *A61M 25/06* | (2006.01) |
| *A61M 25/04* | (2006.01) |

(52) U.S. Cl.
CPC ....... *A61M 25/0023* (2013.01); *A61F 2/2427* (2013.01); *A61F 2/95* (2013.01);
(Continued)

(58) Field of Classification Search
CPC .. A61F 2/24; A61F 2/2436; A61F 2/95; A61F 2/966; A61M 25/00;
(Continued)

(56) References Cited

U.S. PATENT DOCUMENTS

| | | |
|---|---|---|
| 4,601,713 A | 7/1986 | Fuqua |
| 4,710,181 A | 12/1987 | Fuqua |
| | (Continued) | |

FOREIGN PATENT DOCUMENTS

| | | |
|---|---|---|
| EP | 0103546 A1 | 3/1984 |
| EP | 0592410 B1 | 10/1995 |
| | (Continued) | |

OTHER PUBLICATIONS

510K Premarket Notification, Jun. 22, 2018.
BSX Structural Heart Update 2018.

*Primary Examiner* — George J Ulsh
(74) *Attorney, Agent, or Firm* — Meunier Carlin Curfman LLC; Joel B. German

(57) ABSTRACT

Disclosed herein are expandable introducer sheaths and methods of making and using the same. The sheaths minimize trauma to a patient's vasculature by allowing for temporary expansion of a portion of the sheath to accommodate passage of a delivery system for a cardiovascular device, then return to a non-expanded state after the passage of the device. The sheath includes an elongated annular member having longitudinally extending channels that facilitate the sheath's temporary expansion. The channels are positioned in such a way that, upon expansion, they enable the movement of protruding contact surfaces toward the inner and outer surfaces of the annular member, reducing friction between the surface and the passing device. Some embodiments of the expandable sheath include an elastic outer layer that pushes the protruding contact surfaces back towards their original positions after the passage of the device.

14 Claims, 10 Drawing Sheets

(52) U.S. Cl.
CPC ......... *A61M 25/0662* (2013.01); *A61M 25/04* (2013.01); *A61M 2025/0024* (2013.01); *A61M 2025/0681* (2013.01)

(58) Field of Classification Search
CPC .......... A61M 25/0023; A61M 25/0662; A61M 2025/0024; A61M 25/04; A61M 2025/0681
See application file for complete search history.

(56) References Cited

U.S. PATENT DOCUMENTS

| | | | |
|---|---|---|---|
| 4,738,666 A | 4/1988 | Fuqua | |
| 4,921,479 A | 5/1990 | Grayzel | |
| 5,104,388 A | 4/1992 | Quackenbush | |
| 5,318,588 A | 6/1994 | Horzewski et al. | |
| 5,320,611 A | 6/1994 | Bonutti et al. | |
| 5,501,667 A | 3/1996 | Verduin, Jr. | |
| 5,674,240 A | 10/1997 | Bonutti et al. | |
| 5,810,776 A | 9/1998 | Bacich et al. | |
| 5,817,100 A | 10/1998 | Igaki | |
| 5,997,508 A | 12/1999 | Lunn et al. | |
| 6,080,141 A | 6/2000 | Castro et al. | |
| 6,090,072 A | 7/2000 | Kratoska et al. | |
| 6,090,136 A | 7/2000 | McDonald et al. | |
| 6,190,357 B1 | 2/2001 | Ferrari et al. | |
| 6,312,443 B1 | 11/2001 | Stone | |
| 6,346,092 B1 | 2/2002 | Leschinsky | |
| 6,358,238 B1 | 3/2002 | Sherry | |
| 6,443,979 B1 | 9/2002 | Stalker et al. | |
| 6,494,860 B2 | 12/2002 | Rocamora et al. | |
| 6,632,236 B2 | 10/2003 | Hogendijk | |
| 6,652,492 B1 | 11/2003 | Bell et al. | |
| 6,814,715 B2 | 11/2004 | Bonutti et al. | |
| 6,899,727 B2 | 5/2005 | Armstrong et al. | |
| 7,438,712 B2 | 10/2008 | Chouinard | |
| 7,591,832 B2 | 9/2009 | Eversull et al. | |
| 7,655,016 B2 | 2/2010 | Demarais et al. | |
| 7,665,016 B2 | 2/2010 | Behrens et al. | |
| 7,678,128 B2 | 3/2010 | Boyle et al. | |
| 7,713,193 B2 | 5/2010 | Nance et al. | |
| 7,762,995 B2 | 7/2010 | Eversull et al. | |
| 7,766,820 B2 | 8/2010 | Core | |
| 7,780,692 B2 | 8/2010 | Nance et al. | |
| 7,785,360 B2 | 8/2010 | Freitag | |
| 7,837,692 B2 | 11/2010 | Mulholland et al. | |
| 7,892,203 B2 | 2/2011 | Lenker et al. | |
| 7,927,309 B2 | 4/2011 | Palm | |
| 7,963,952 B2 | 6/2011 | Wright, Jr. et al. | |
| 8,034,072 B2 | 10/2011 | Nguyen et al. | |
| 8,048,034 B2 | 11/2011 | Eversull et al. | |
| 8,090,936 B2 | 1/2012 | Fallon et al. | |
| 8,092,481 B2 | 1/2012 | Nance et al. | |
| 8,252,015 B2 | 8/2012 | Leeflang et al. | |
| 8,282,664 B2 | 10/2012 | Nance et al. | |
| 8,414,645 B2 | 4/2013 | Dwork et al. | |
| 8,562,559 B2 | 10/2013 | Bishop et al. | |
| 8,562,673 B2 | 10/2013 | Yeung et al. | |
| 8,652,203 B2 | 2/2014 | Quadri et al. | |
| 8,668,668 B2 | 3/2014 | Bishop et al. | |
| 8,690,936 B2 | 4/2014 | Nguyen et al. | |
| 8,790,387 B2 | 7/2014 | Nguyen et al. | |
| 9,044,577 B2 | 6/2015 | Bishop et al. | |
| 9,192,751 B2 | 11/2015 | Macaulay et al. | |
| 9,192,752 B2 | 11/2015 | Leeflang et al. | |
| 9,254,374 B2 | 2/2016 | Thorstenson et al. | |
| 9,259,813 B2 | 2/2016 | Heideman et al. | |
| 9,301,840 B2 | 4/2016 | Nguyen et al. | |
| 9,301,841 B2 | 4/2016 | Nguyen et al. | |
| 9,320,508 B2 | 4/2016 | Carroux | |
| 9,393,041 B2 | 7/2016 | Barker et al. | |
| 9,642,704 B2 | 5/2017 | Tuval et al. | |
| 9,788,944 B2 | 10/2017 | Daly et al. | |
| 9,907,931 B2 | 3/2018 | Birmingham et al. | |
| 2002/0032459 A1 | 3/2002 | Horzewski et al. | |
| 2002/0123793 A1 | 9/2002 | Schaldach et al. | |
| 2003/0004537 A1 | 1/2003 | Boyle et al. | |
| 2004/0087968 A1 | 5/2004 | Core | |
| 2004/0122415 A1 | 6/2004 | Johnson | |
| 2005/0080430 A1 | 4/2005 | Wright et al. | |
| 2005/0085842 A1 | 4/2005 | Eversull et al. | |
| 2005/0125021 A1 | 6/2005 | Nance et al. | |
| 2006/0020321 A1 | 1/2006 | Parker | |
| 2006/0135962 A1 | 6/2006 | Kick et al. | |
| 2006/0135981 A1 | 6/2006 | Lenker et al. | |
| 2006/0217755 A1 | 9/2006 | Eversull et al. | |
| 2007/0021768 A1 | 1/2007 | Nance et al. | |
| 2007/0074805 A1 | 4/2007 | Leeflang et al. | |
| 2007/0087148 A1 | 4/2007 | Okushi et al. | |
| 2008/0004521 A1 | 1/2008 | Hundley et al. | |
| 2008/0004571 A1 | 1/2008 | Voss | |
| 2008/0114331 A1 | 5/2008 | Holman et al. | |
| 2008/0243081 A1 | 10/2008 | Nance et al. | |
| 2010/0094209 A1 | 4/2010 | Drasler et al. | |
| 2010/0094392 A1 | 4/2010 | Nguyen et al. | |
| 2010/0198160 A1 | 8/2010 | Voss | |
| 2011/0112567 A1 | 5/2011 | Lenker et al. | |
| 2011/0190697 A1 | 8/2011 | Farnan | |
| 2011/0251681 A1 | 10/2011 | Shipley et al. | |
| 2012/0116439 A1 | 5/2012 | Ho | |
| 2012/0158033 A1 | 6/2012 | Deal et al. | |
| 2012/0323180 A1 | 12/2012 | Chebator et al. | |
| 2013/0131718 A1 | 5/2013 | Jenson et al. | |
| 2013/0178711 A1 | 7/2013 | Avneri et al. | |
| 2013/0231735 A1 | 9/2013 | Deem et al. | |
| 2013/0281787 A1 | 10/2013 | Avneri et al. | |
| 2014/0121629 A1 | 5/2014 | Macaulay et al. | |
| 2014/0236122 A1 | 8/2014 | Anderson et al. | |
| 2014/0236123 A1 | 8/2014 | Birmingham et al. | |
| 2014/0379067 A1 | 12/2014 | Nguyen et al. | |
| 2015/0182723 A1 | 7/2015 | Leeflang et al. | |
| 2015/0238178 A1 | 8/2015 | Carroux | |
| 2015/0265798 A1 | 9/2015 | Nihonmatsu et al. | |
| 2015/0320971 A1 | 11/2015 | Leeflang et al. | |
| 2016/0074067 A1 | 3/2016 | Furnish et al. | |
| 2016/0135840 A1 | 5/2016 | Kick et al. | |
| 2016/0213882 A1 | 7/2016 | Fitterer et al. | |
| 2016/0296332 A1 | 10/2016 | Zhou et al. | |
| 2016/0296730 A1 | 10/2016 | Zhou et al. | |
| 2017/0014157 A1* | 1/2017 | Coyle | A61B 17/3439 |
| 2017/0072163 A1 | 3/2017 | Lim et al. | |
| 2017/0209133 A1 | 7/2017 | Ciulla et al. | |
| 2017/0252062 A1 | 9/2017 | Fitterer et al. | |
| 2018/0161064 A1 | 6/2018 | Fitterer et al. | |
| 2018/0199960 A1 | 7/2018 | Anderson et al. | |
| 2018/0229000 A1 | 8/2018 | Anderson et al. | |

FOREIGN PATENT DOCUMENTS

| | | |
|---|---|---|
| EP | 1139889 A1 | 10/2001 |
| EP | 1694398 A2 | 8/2006 |
| EP | 1793881 A2 | 6/2007 |
| EP | 1804860 A2 | 7/2007 |
| EP | 2101661 A1 | 9/2009 |
| EP | 2288403 A2 | 3/2011 |
| EP | 2475417 A2 | 7/2012 |
| EP | 2862590 A1 | 4/2015 |
| EP | 2911729 A1 | 9/2015 |
| EP | 2995268 A1 | 3/2016 |
| JP | 2012040145 A | 3/2012 |
| WO | 2004037333 A1 | 5/2004 |
| WO | 2008147964 A1 | 12/2008 |
| WO | 2009035745 A1 | 3/2009 |
| WO | 2013044942 A1 | 4/2013 |
| WO | 2014140093 A1 | 9/2014 |
| WO | 202016118789 A1 | 7/2016 |
| WO | 202017040774 A1 | 3/2017 |
| WO | 2018148488 A1 | 8/2018 |

* cited by examiner

EXPANDABLE SHEATH

RELATED APPLICATIONS

This application claims the benefit of priority to U.S. Provisional Application No. 62/449,454, filed Jan. 23, 2017, which is incorporated herein by reference.

FIELD

The present application is directed to a sheath for use with catheter-based technologies for repairing and/or replacing heart valves, as well as for delivering an implant, such as a prosthetic valve to a heart via the patient's vasculature.

BACKGROUND

Endovascular delivery catheter assemblies are used to implant prosthetic devices, such as a prosthetic heart valve, at locations inside the body that are not readily accessible by surgery or where less invasive surgery is desirable. For example, aortic, mitral, tricuspid, and/or pulmonary prosthetic valves can be delivered to a treatment site using minimally invasive surgical techniques, including transcatheter delivery methods.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for the prosthetic implant, such as a heart valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths reduce the overall profile of the sheath to reduce risk of damage to the vessel. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque. The addition of radially expanding properties can also hinder a practitioner's ability to push the sheath without it bending or kinking. Thus, there remains a need for further improvements in introducer sheaths for endovascular systems used for implanting heart valves and other prosthetic devices.

SUMMARY

Disclosed herein are expandable introducer sheaths and methods of making and using the same. The sheaths are adapted to temporarily expand a portion of the sheath to allow for the passage of a delivery system for a cardiovascular device, then return to a non-expanded state after the passage of the system. The sheath includes an elongated annular member through which the cardiovascular device and its delivery system pass. The annular member has longitudinally extending channels that facilitate the sheath's expansion. The channels are positioned in such a way that, upon expansion, they enable the movement of longitudinally extending contact surfaces toward the inner and outer surfaces of the annular member, reducing friction between the surface and the passing device. Some embodiments of the expandable sheath include an elastic outer layer that pushes the contact surfaces back towards their original positions after the passage of the device. Methods of making an expandable sheath tip are also included.

Disclosed herein are expandable sheaths including an elongated annular member that has an inner and outer surface. The annular member also include a bridge member extending between opposing first and second base members spaced around the circumference of the annular member. The expandable sheath is radially movable between an expanded state and a non-expanded state. In the non-expanded state, the annular member includes a first and second longitudinally extending channel. The first longitudinally extending channel is defined between the bridge member the first base member and extends inwardly from the outer surface of the sheath towards the annular member's longitudinal axis. The second longitudinally extending channel is defined between the bridge member and the second base member and extends outwardly from the inner surface of the sheath away from the longitudinal axis of the annular member. In the expanded state, the bridge member extends in a direction around the circumference of the annular member increasing a distance between the first and second base members.

In some embodiments of the expandable sheath, the expanded diameter of the annular member is greater than the non-expanded diameter of the annular member.

In some embodiments of the expandable sheath the orientation of the first and second base members changes when the annular member moves between the expanded and non-expanded state. For example, the orientation of the first and second base members can rotate about a longitudinal axis of each of the respective base members when the annular member is moved between the expanded and non-expanded state.

Some embodiments of the expandable sheath include the first and second base members having a contact edge that defines the inner diameter of the annular member in the expanded state.

In some embodiments, the bridge member extends in a direction around a circumference of the annular member in the expanded state. For example, the first and second base members can extend in a direction around a circumference of the annular member in the expanded and non-expanded state, and at least a portion of the bridge member can extend in a direction towards the longitudinal axis of annular member in the non-expanded state and around the circumference of the annular member in the expanded state.

In some embodiments the first and second base members define a rectilinear shape in cross-section. The bridge member can define an S-shape in cross-section. In some embodiments, the bridge member can define an arcuate shape in cross-section.

Some embodiments of the expandable sheath includes an outer layer extending over the annular member, the outer layer can comprise a material having a higher elastic modulus than the annular member and the annular member can comprise a material having greater lubricity than the outer layer.

Also disclosed is an expandable sheath including an elongated annular member movable between a non-expanded and expanded state. The annular member includes base members spaced around a circumference of the annular member, and bridge members extending between opposing pairs of base members. In the non-expanded state the annular member includes inwardly and outwardly extending channels that extend towards and away from the longitudinal axis of the annular member, respectively. The inwardly and outwardly extending channels can be defined between the base and bridge members. In the expanded state the diameter of the annular member is increased and a spacing between opposing based members is increased from the non-expanded state diameter and spacing.

In some embodiments of the expandable sheath, one inwardly extending channel and one outwardly extending channels is provided at opposing ends of a corresponding one of the bridge members. In some embodiments, in the expanded state the depth of each of the inwardly and outwardly extending channels, in a radial direction, is decreased compared to a depth of each of the channels in the non-expanded state.

In some embodiments of the expandable sheath the base members include a first, second and third base member and the bridge members include a first and second bridge member. The first bridge member extends between the first and second base members, and the second bridge member extends between the second and third base members.

Also disclosed is a method of making an expandable sheath. The method includes coextruding a tube comprising a first material and a second material. The first material defines the elongated annular member having an outer surface and an inner surface. The first material further defines a first and second set of longitudinally extending channels. The first set of longitudinally extending channels extend inwardly from an outer surface of the elongated member towards the longitudinal axis of the annular member. The second set of longitudinally extending channels extend outwardly from an inner surface of the annular member away from the longitudinal axis. The second material defines a first set of longitudinally extending ribbons extending within the first set of channels and a second set of longitudinally extending ribbons extending within the second set of channels. Each ribbon of a selected set is positioned circumferentially between ribbons of the other set.

In some embodiments, the method of making an expandable sheath can further include coextruding a third material in contact with a portion of the first material and a portion of the second material, wherein the third material adheres to both the first material to the second material. The third material can be located between a portion of the first and second material within the first and second set of channels.

In some embodiments, the method of making an expandable sheath can further include adding a taper tube to the coextrusion.

In some embodiments, the method of making an expandable sheath can further include removing the second material and exposing the first and second set of longitudinally extending channels upon removal of the second sacrificial material.

In some embodiments, the method can further include covering the annular member with an outer layer comprising a material having a higher elastic modulus than the annular member.

Also disclosed is a method of delivering a cardiovascular prosthetic device. The method includes positioning an expandable sheath at an implantation site within the vascular system of a patient, introducing a prosthetic device into a lumen of the expandable sheath, advancing a cardiovascular prosthetic device through the lumen of the expandable sheath, exerting a radially outward force on an inner surface of the sheath with the cardiovascular prosthetic device, widening longitudinally extending channels provided circumferentially around the inner and outer surfaces of the sheath and moving longitudinally extending contact surfaces toward the inner and outer surfaces of the sheath, thereby expanding a portion of the sheath a a location of the radially outward force. The method further includes at least partially collapsing the expanded portion of the sheath after the device has passed through the expanded portion. In some embodiments, the cardiovascular prosthetic device is a prosthetic heart valve.

In some embodiments, the method of delivering a cardiovascular prosthetic device can further include moving the contact surfaces away from the inner and outer surfaces of the annular member after passage of the cardiovascular prosthetic device using an outer layer of the expandable sheath.

Also disclosed is a method of making a distal tip of an expandable sheath. The method includes pinching a portion of the distal end of a tube to create a longitudinally extending outer crease, folding the pinched portion over an outer surface of a distal end of the tube in a circumferential direction to create a longitudinally extending flap bounded by the outer crease and a longitudinally extending inner crease, cutting the inner crease of the longitudinally extending flap in a longitudinal direction from the distal edge of the tube to a proximally spaced point along the longitudinal axis of the tube to create a longitudinally extending inner edge, cutting the longitudinally extending flap at the proximally spaced point in a circumferential direction from the outer crease to the longitudinal cut at the inner crease, extending the inner edge of the longitudinally extending flap in a circumferential direction around the outer surface of the distal end of the tube, and adhering the cut inner crease to the outer surface of the distal end of the tube to create the distal tip. Some embodiments of the method further include covering the cut distal end of the tube with an outer jacket and reflowing the tube with the outer jacket to create the sealed distal tip.

DESCRIPTION OF DRAWINGS

In the drawings, like reference numbers and designations in the various drawings indicate like elements.

DETAILED DESCRIPTION

Figure 1:
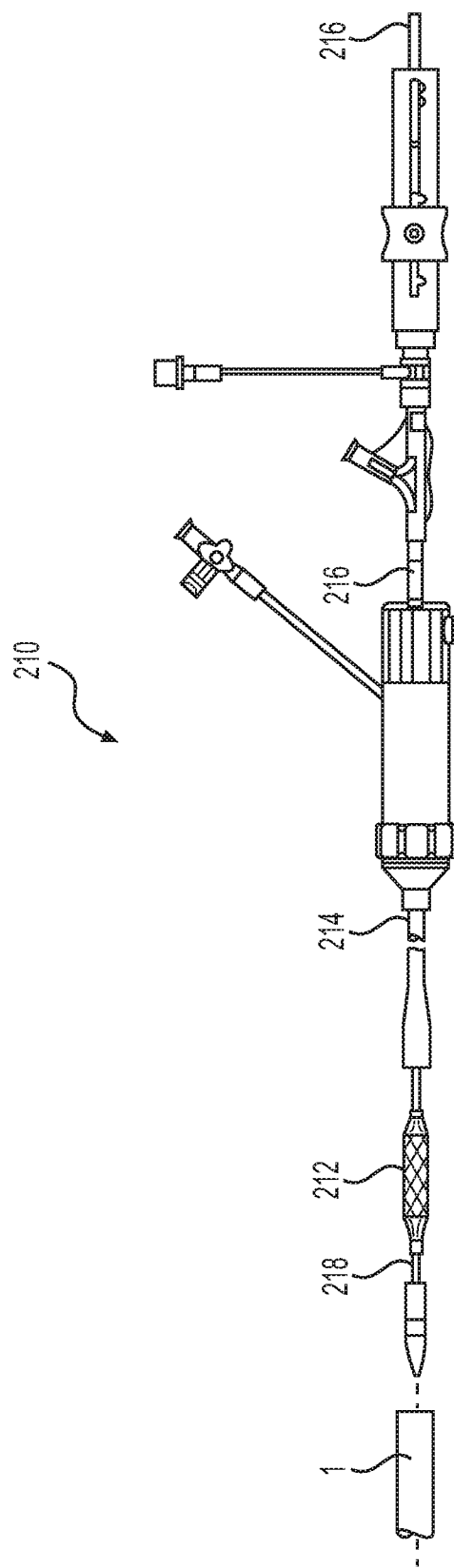
FIG. 1 is an elevation view of an expandable sheath along with an endovascular delivery system for implanting a prosthetic heart valve.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Disclosed herein are expandable introducer sheaths and methods of making and using the same. As will be described in further detail below, the expandable sheaths 1 are adapted to allow for temporary expansion of a portion of the sheath to accommodate the passage of a delivery system for a cardiovascular device, then return to a non-expanded state, or "recover" after the passage of the delivery system and device.

FIG. 1 illustrates a sheath 1 according to the present disclosure in use with a representative delivery apparatus 210 for delivering a prosthetic device 212, such as a tissue heart valve, to a patient. The apparatus 210 can include a steerable guide catheter 214 (also referred to as a flex catheter), a balloon catheter 216 extending through the guide catheter 214, and a nose catheter 218 extending through the balloon catheter 216. The guide catheter 214, the balloon catheter 216, and the nose catheter 218 in the illustrated embodiment are adapted to slide longitudinally relative to each other to facilitate delivery and positioning of the valve 212 at an implantation site in a patient's body, as described in detail below. Generally, a sheath 1 is inserted into a vessel, such as the transfemoral vessel, passing through the skin of patient, such that the distal end of the sheath 1 is inserted into the vessel. Sheath 1 can include a hemostasis valve at the opposite, proximal end of the sheath. The delivery apparatus 210 can be inserted into the sheath 1, and the prosthetic device 212 can then be delivered and implanted within patient.

The expandable introducer sheath 1 is adapted to allow for temporary radial expansion of a portion of the sheath to accommodate the passage of a delivery system for a cardiovascular device (e.g., prosthetic heart valve 212) and to then return to a non-expanded state after the passage of the delivery system with its prosthetic device. The expandable sheath 1 includes an elongated annular member 10 through which the delivery system and prosthetic heart valve 212 pass. As will be described in more detail below, the annular member 10 of the expandable sheath 1 can include longitudinally extending channels 12, 14 that facilitate the sheath's expansion for passage of the prosthetic heart valve 212. The channels 12, 14 are positioned such that upon expansion of the annular member 10 certain contact surfaces 22, 24 are brought into contact with adjacent surfaces of the delivery apparatus 210, thereby reducing friction between the annular member 10 and the passing structure. In some embodiments, the radial expansion of the expandable annular member 10 at any given portion along its length is due to the ability of base 20 and/or bridge members 30 of the annular member 10 to rotate. The rotation of these sections reduces the surface/contact area of the annular member 10 thereby reducing friction with the passing structure. The expandable sheath 1 can include an elastic outer layer 50. In some embodiments, the outer layer 50 can compress the annular member 10 towards a non-expanded configuration.

Figure 2A:
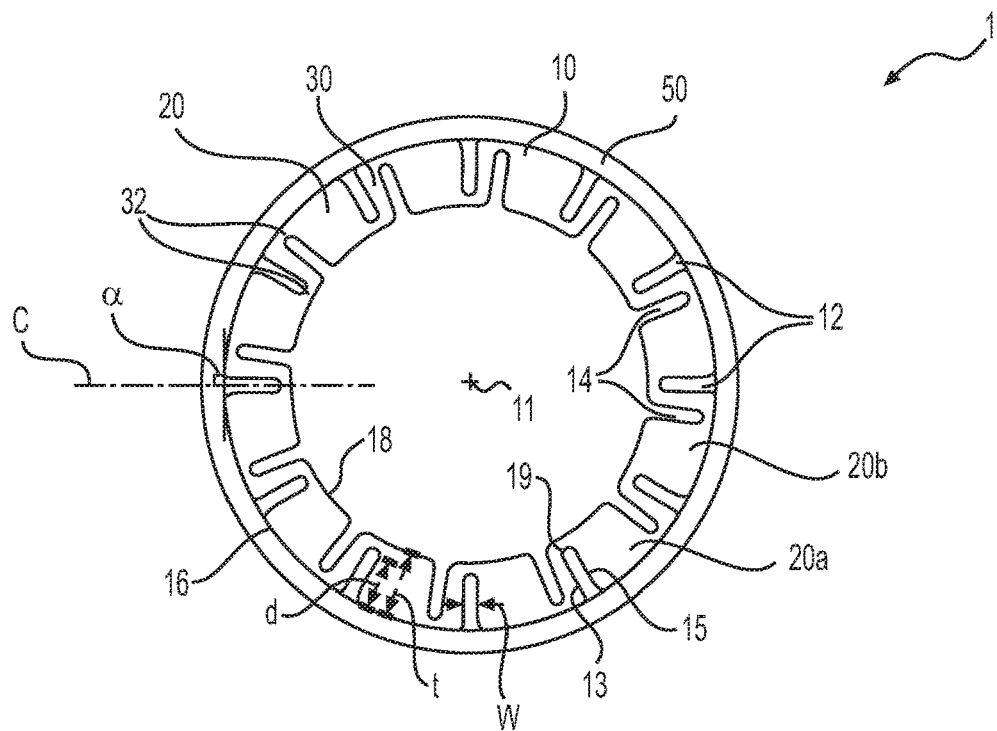
FIG. 2A shows a cross sectional view of an example expandable sheath in the non-expanded state.
Figure 2B:
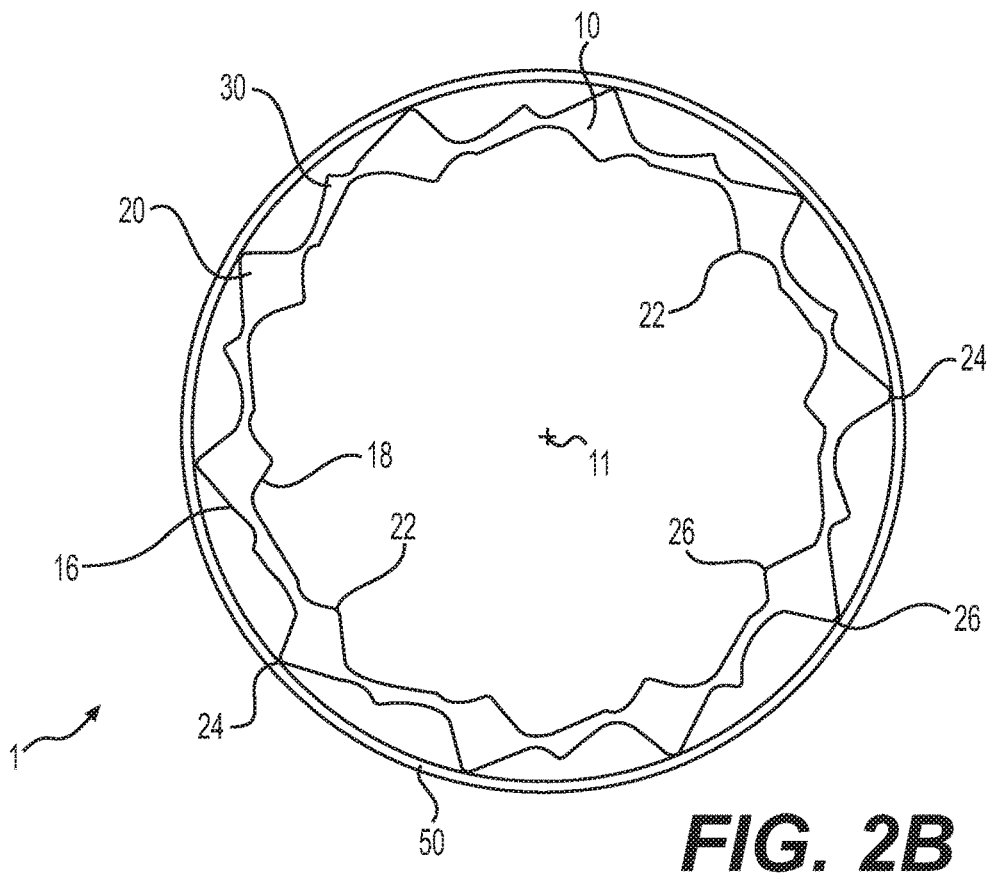
FIG. 2B shows the expandable sheath of FIG. 2A in the expanded state.

FIGS. 2A and 2B show a cross-section of an example expandable sheath 1 in an expanded (FIG. 2A) and a non-expanded (FIG. 2B) state. The non-expanded sheath 1 includes an inner annular member 10 and an outer layer 50. The outer layer 50 can be constructed from an elastic material that allows for temporary radial expansion of a portion of the outer layer 50 corresponding to the temporary radial expansion of the annular member 10 to accommodate the passage of the delivery system for a cardiovascular device (e.g., prosthetic heart valve 212). After passage of the delivery system with its prosthetic device, the annular member 10 and outer layer 50 return to a non-expanded state (FIG. 2B). As illustrated in FIG. 2A, the annular member 10 includes a plurality of base members 20 arranged around the circumference of the annular member 10 and bridge members 30 extending between opposing pairs of base members 20 (e.g., base member 20a and base member 20b). As illustrated in FIG. 2A, the base members 20 can define a rectilinear shape in cross-section. The base members 20 can include an outer edge that define the outer surface/diameter 16 of the annular member 10 and an inner edge that define the inner surface/diameter 18. Base members 20 can include side walls 15 that extend radially between the inner and outer edges. As illustrated in FIG. 2A, the outer edge has a longer length (around the circumference of the annular member 10) than the inner edge. The side walls 15 can meet the inner and outer edges at a curve (illustrated) or angle. The side walls 15 can terminate at the bridge member 30. As provided in FIG. 2A, the side walls 15 can meet the bridge members 30 at a curve. In other example annular members 10 (see e.g., FIG. 6A) the side wall of the base member 20 can meet the bridge member 30 at a straight or angled edge/joint. It is further contemplated that the base members 20 can define any regular or irregular shape in cross-section including, for example, square, rectangle, trapezoidal, circular, and oval. Likewise, bridge members 30 can define any regular or irregular shape. As provided in FIG. 2A, in the unexpanded state the bridge members 30 define a generally S-shape cross-section. That is, in cross-section, the bridge members 30 of FIG. 2A can include a relatively (radially) elongate shape that extends between bends (at joints 32) where the bridge member 30 couples to the adjacent base member 20. The bends bracket the ends of the elongate portion and serve as the connection to either the radially inward corner or radially outward corner of adjacent base members. The elongate portion of the bridge member 30 can also widen in the outward radial direction. As will be explained in more detail below, during expansion of the annular member 10 the shape of the base member 20 and/or bridge member 30 changes or otherwise deforms.

As illustrated in FIG. 2A, in the non-expanded state, the annular member 10 includes longitudinally extending channels 12, 14. Inward extending channels 12 extend radially inward from the outer surface/diameter 16 of the annular member 10 towards its longitudinal axis 11. The inward extending channels 12 are defined between a base member 20 and an adjacent bridge member 30. The outward extending channels 14 extend radially outward from the inner surface/diameter 18 of the annular member 10 in a radial direction away from the longitudinal axis 11 and are similarly defined between a base member 20 and an adjacent bridge member 30.

The inward and outward extending channels 12, 14 alternate in inward versus outward directionality, such that each channel of a selected set/direction is positioned circumferentially between two channels of the other set/direction (i.e., an inward extending channel 12 is position circumferentially between two outward extending channels 14).

As depicted in FIG. 2A, the inward and outward extending channels 12, 14 extend radially with respect to the longitudinal axis 11 of the annular member 10. For example, the centerline (c) of each of the inward and outward extending channels 12, 14 can create a 90-degree angle (a) with a line tangent to the diameter of the annular member 10 proximate the opening of the channel.

The inward and outward extending channels 12, 14 extend a certain depth (d) into the wall thickness (t) of the annular member 10. For example, as illustrated in FIG. 2A, the inward and outward extending channels 12, 14 can have a depth greater than 50% of the wall thickness (t) of the annular member 10. Though not illustrated, it is contemplated that the depth of the inward and outward extending channels 12, 14 can also vary around the annular member 10.

The inward and outward extending channels 12, 14 can also define a width (w) measured along the length/depth of the channel. The width (w) can be defined between the sidewall of the corresponding bridge member 30 and base member 20, i.e., side wall 13 and side wall 15. As illustrated in FIG. 2A, the width (w) of each channel can be uniform around the annular member 10. It is also contemplated that the width (w) of different channels can vary around the annular member 10. The width (w) of the inward and outward extending channels 12, 14 can remain constant (see FIG. 2A) or vary along the depth (d) of the channel.

The shape of the inward and outward extending channels 12, 14 can remain constant or vary around the annular member 10. As depicted in FIG. 2A, each of the inward and outward extending channels 12, 14 have two substantially parallel and straight sides (defined by side wall 13 and side wall 15) that terminate at a rounded end 19. It is contemplated that the shape of inward and outward extending channels 12, 14 can define any regular or irregular shape and that the shape of each inward and outward extending channel 12, 14 can vary (or remain constant) around the annular member 10.

In the embodiment shown in FIG. 2A, the inward and outward extending channels 12, 14 are evenly distributed around the circumference of the annular member 10 and are similar in size and shape. While it is contemplated that the size and spacing of the base members 20, bridge members 30 and corresponding inward and outward extending channels 12, 14 can vary, even spacing and uniform size and shape help to prevent tearing of the annular member 10 during expansion. For example, during expansion (shown in FIG. 2B) tension is distributed to many points around the circumference of the annular member 10 and not focused at a single location. This distribution of tension reduces the risk of tearing the annular member 10.

As described above, the annular member 10 and elastic outer layer 50 of the sheath 1 are designed to locally expand as the prosthetic device 212 is passed through the interior lumen of the sheath 1 and then substantially return to their original shape once the prosthetic device has passed through that portion of the sheath. That is, in the non-expanded state the outer diameter of the annular member 10 and outer layer 50 can be substantially constant across the length of the sheath 1 from the proximal end 3 to the distal end 5. As the prosthetic device 212 passes through the interior lumen of the sheath 1, the portion of the annular member 10 and outer layer 50 proximate the prosthetic device 212 expand radially, with the remaining length/portion of the annular member 10 and outer layer 50 in a substantially non-expanded state. Once the device has passed through a portion of the lumen of the sheath 1, that portion of the sheath 1 can substantially return to its original shape and size. FIG. 2B illustrates the annular member 10 and outer layer 50 in an expanded state. In the expanded state the outer diameters of the annular member 10 and elastic outer layer 50 are greater than the non-expanded diameters of the annular member 10 and outer layer 50.

To achieve expansion, the orientation of the base members 20 and bridge members 30 changes. As illustrated in FIG. 2B, the base members 20 rotate during expansion of the annular member 10. For example, the base members 20 rotate with respect to the central axis of each corresponding base member 20. Similarly, the bridge members 30 rotate and flex at joints 32 to extend in a direction around the circumference of the annular member 10, thereby increasing the distance/spacing between adjacent base members 20 and widening/changing the shape of each of the intervening inward and outward extending channels 12, 14. The bridge members 30 can be constructed from a flexible material to accommodate flexing at joints 32 and/or lengthening/deformation during expansion of the annular member 10 and then substantially return to the original, non-expanded shape/configuration. The base members 20 can be constructed from a same or different material than the bridge members 30. Accordingly, it is also contemplated that the base members 20 can flex and deform during expansion and contraction of the annular member 10.

As illustrated in FIG. 2B, in the expanded state the orientation of the base members 20 and bridge members 30 changes. Contact surfaces 22, 24 provided on the base members 20 now define the inner and outer diameters of the annular member 10, respectively. In the expanded state, the contact surfaces 24 define the inner diameter of the outer layer 50. The contact surfaces 22 extend towards the interior of the annular member 10 and reduce the contact surface area between the annular member 10 and the passing device, thereby lowering the coefficient of friction/resistance between the inner surface 18 of the annular member 10 and the passing device. The contact surfaces 22, 24 can define rounded/curved ends 26 or linear/angled ends 28 when viewed in cross-section. For example, the contact surfaces 22, 24 of the expanded embodiments shown in FIGS. 2B, 3B, 4B, 5B and 6C include rounded ends 26 in cross-section.

Figure 7A:
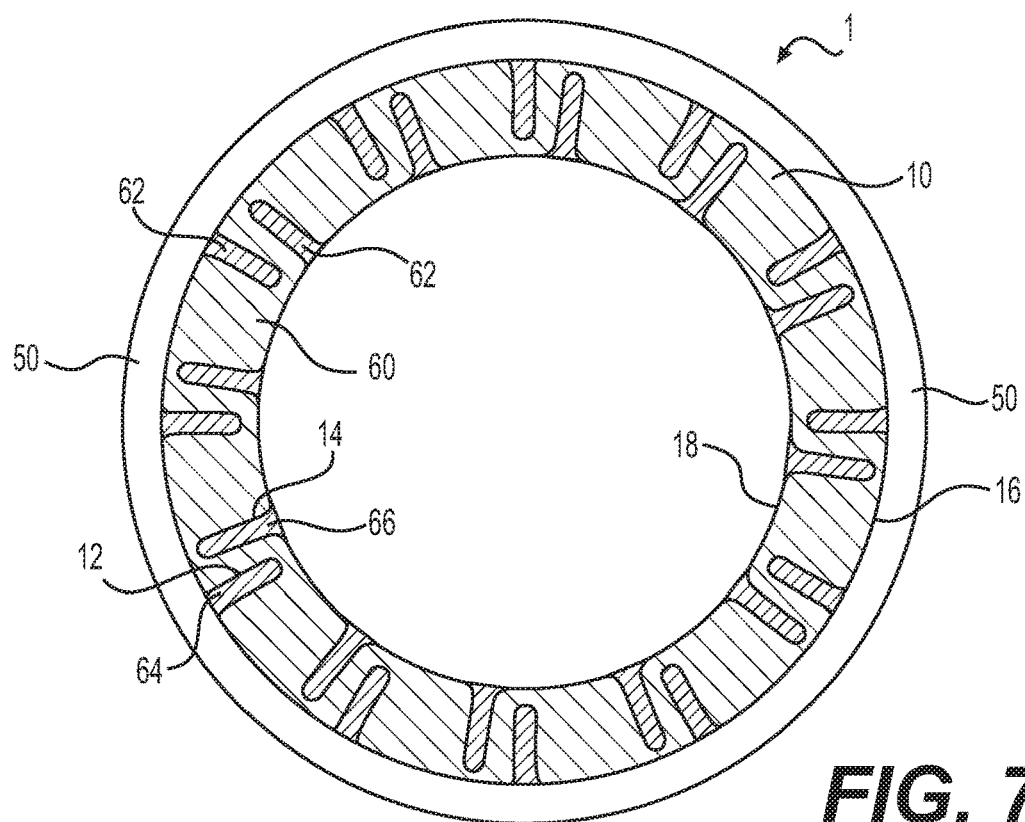
FIG. 7A shows a cross sectional view of an example expandable sheath during an intermediate processing step.
Figure 7B:
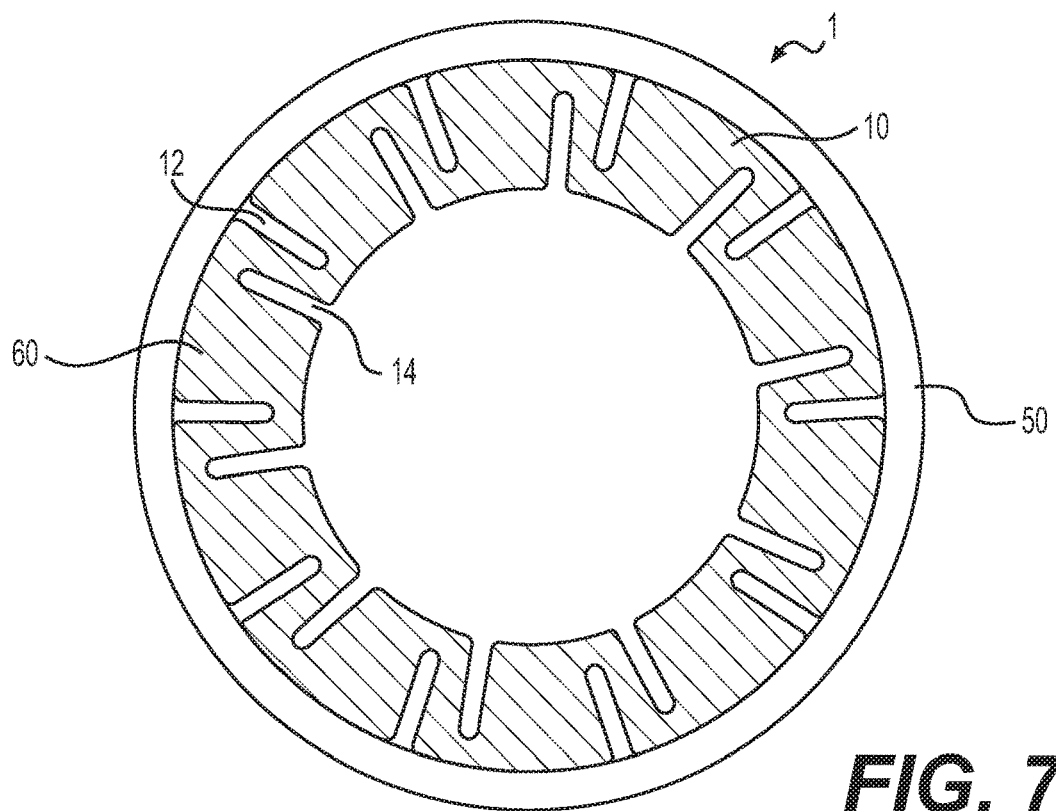
FIG. 7B shows the expandable sheath of FIG. 7A in a non-expanded state, after removal of a sacrificial material.

In another example, the expanded annular member depicted in FIG. 7B includes both angled ends 28 and rounded ends 26 at the contact surfaces 22, 24. Referring back to FIG. 2B, the shape of the rounded ends 26, including the radii of curvature, can be constant across all base members 20 of the annular member 10. It is also contemplated that the shape of the rounded ends 26/contact surfaces 22, 24 may vary between base members 20, and vary between contact surface 22 and contact surface 24 of the same base member 20.

In transition back to the non-expanded state, the base members 20 and bridge members 30 move back to their original configuration/orientation. The transition back to the non-expanded state can be facilitated by the inclusion of an elastic outer layer 50 that extends over the elongated annular member 10. The outer layer 50 comprises a material having a higher elastic modulus than the annular member 10, which enables the outer layer 50 to force the annular member 10 back into the non-expanded state after passage of the cardiovascular device. The annular member 10 can be made of a more lubricious material than the outer layer 50. For example, the outer layer 50 can be made of, or incorporate, polyurethane, silicone, and/or rubber, and the annular member 10 can be made of, or incorporate, high density polyethylene, polytetrafluoroethylene, and/or other fluoropolymers.

Figure 3A:
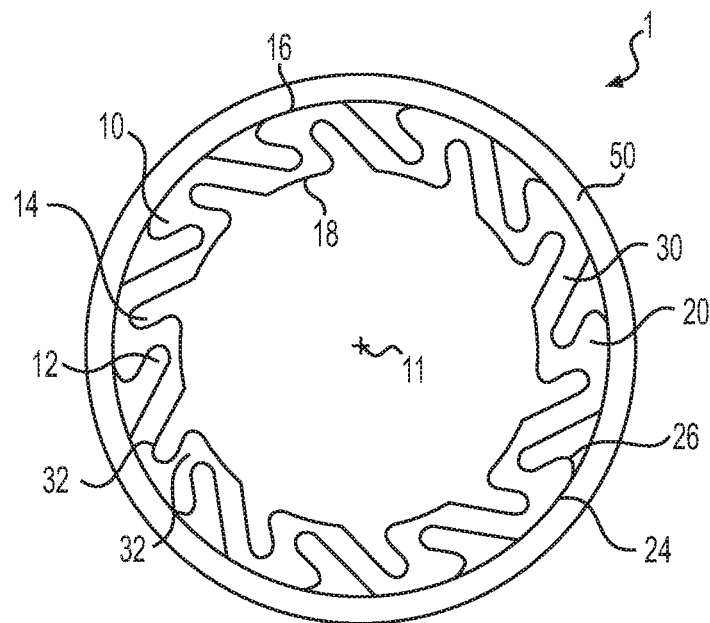
FIG. 3A shows a cross sectional view of an example expandable sheath in the non-expanded state.
Figure 3B:
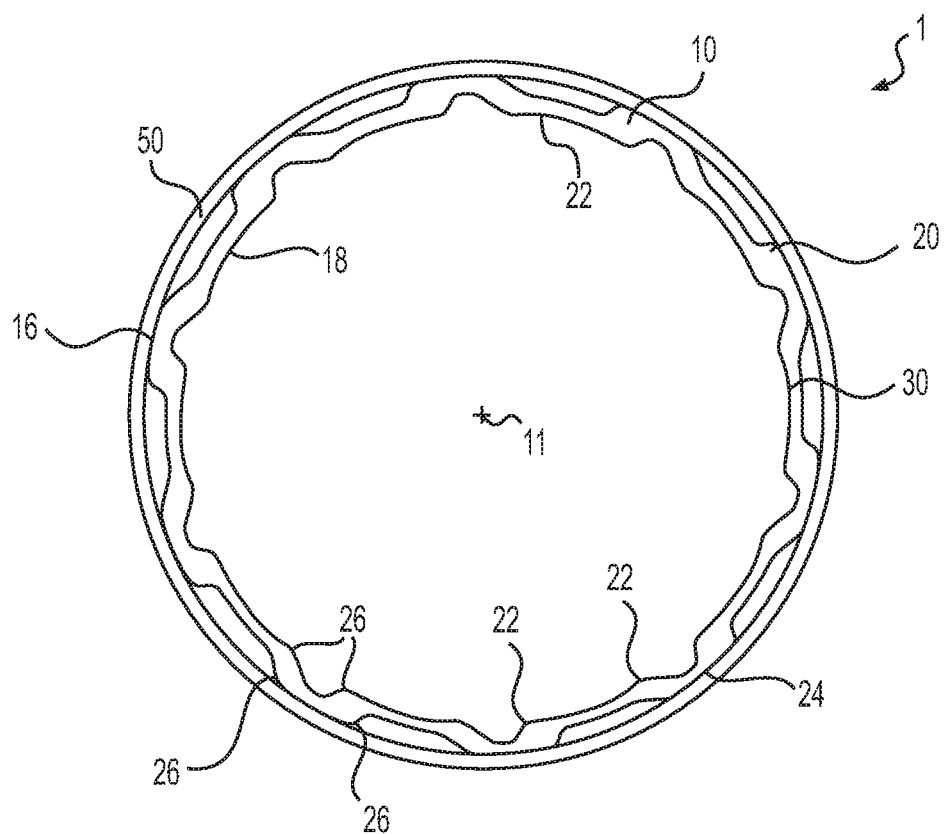
FIG. 3B shows the expandable sheath of FIG. 3A in the expanded state.

FIGS. 3A and 3B depict another example sheath 1 including an annular member 10 and elastic outer layer 50. The annular member 10 has a plurality of base members 20 arranged around the circumference of the annular member 10 and bridge members 30 extending between opposing pairs of base members 20. As illustrated in FIG. 3A, the base members 20 and bridge members 30 can define a curvilinear shape in cross-section. For example, as depicted in FIG. 3A, the base member 20 can define an elongated portion extending around the outer surface/diameter 16 of the annular member and terminating in a rounded end 26 contact surface 24. The bridge 30 can define an elongated member having substantially linear and parallel sides and terminating at a curved end proximate the inner surface/diameter 18 of the annular member 10.

Similar to the annular member 10 depicted in FIG. 2A, in the non-expanded state the annular member 10 of FIG. 3A includes longitudinally extending channels 12, 14 defined between a bridge member 30 and adjacent base member 20 alternating in inward versus outward directionality around the circumference of the annular member 10. The inward extending channels 12 extend inward from the outer surface/diameter 16 of the annular member 10 and the outward extending channels 14 extend outward from the inner surface/diameter 18 of the annular member 10. The inward and outward extending channels 12, 14 can extend inward or outward from the inner/outer surface 16, 18 at an angle, e.g., at an angle other than 90-degrees (with respect to a line tangent to the diameter of the annular member 10 proximate the opening of the channel).

As described above, the annular member 10 and the elastic outer layer 50 of the sheath 1 are designed to locally expand in a radial direction between a non-expanded and an expanded state as the prosthetic device 212 is passed through the interior lumen of the sheath 1. FIG. 3B illustrates the annular member 10 and outer layer 50 in an expanded state. The orientation and/or shape of the base members 20 and bridge members 30 of the annular member 10 change during expansion. As illustrated in FIG. 3B, the base members 20 extend and elongate in a direction around the circumference of the annular member 10 when transitioned to the expanded state. The bridge members 30 change in orientation during expansion. In the non-expanded state the bridge members 30 extend is a direction toward/angled with respect to the longitudinal axis 11/the interior of the annular member 10. Upon expansion of the annular member 10 the bridge members 30 rotate, elongate and/or extend in a direction around the circumference of the annular member 10. For example, the bridge members 30 can flex at joints 32 to facilitate their change in orientation with respect to the base members 20. Upon expansion of the annular member 10, the distance/spacing between adjacent base members 20 increases, widening and changing the shape of the intervening inward and outward extending channels 12, 14 and increasing the overall diameter of the annular member 10 and the outer layer 50.

As illustrated in FIG. 3B, in the expanded state the contact surfaces 22 provided on the base member 20 and/or bridge member 30 define the inner diameter of the annular member 10. Likewise, the contact surface 24 defines the outer diameter of the annular member 10, and the corresponding inner diameter of the outer layer 50 in the expanded state. The outside surface of the outer layer 50 defines the outermost diameter of the combined annular member 10/outer layer 50. Contact surfaces 22 reduce the contact surface area between the annular member 10 and the passing device, thereby lowering the coefficient of friction/resistance between the inner surface 18 and the passing device.

Figure 4A:
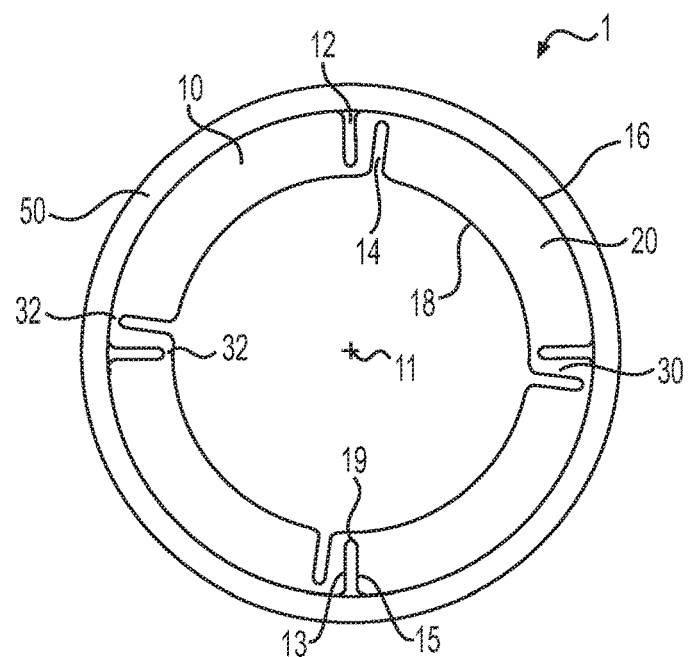
FIG. 4A shows a cross sectional view of an example expandable sheath in the non-expanded state.
Figure 4B:
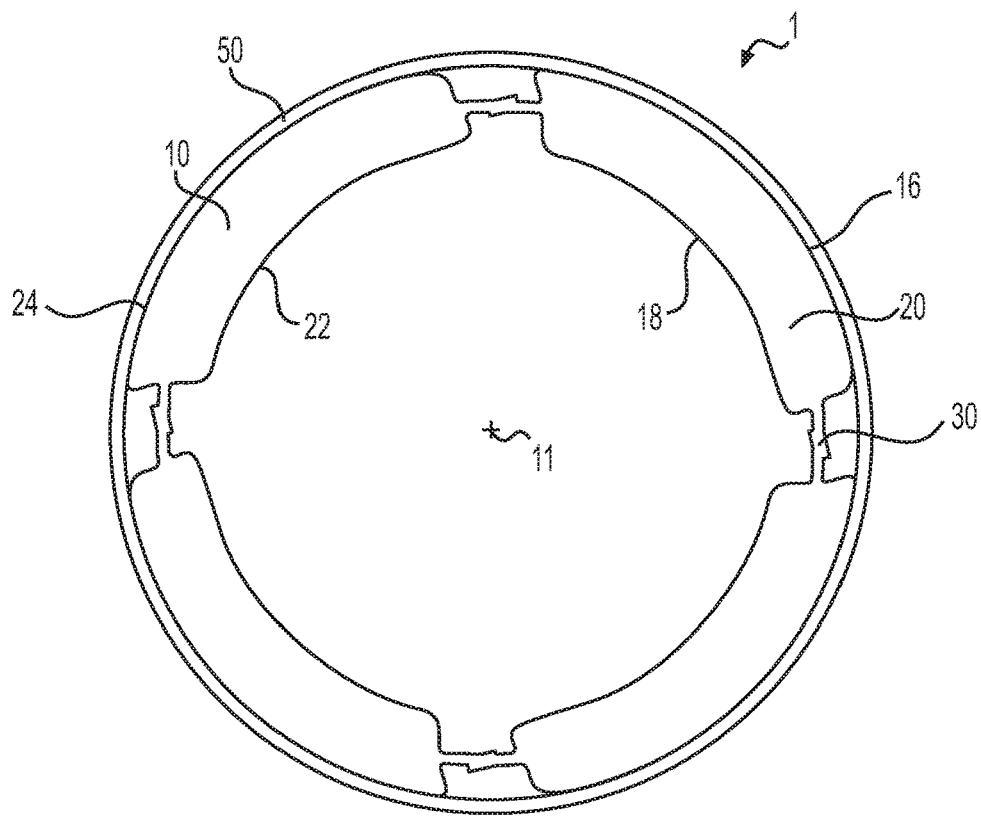
FIG. 4B shows the expandable sheath of FIG. 4A in the expanded state.

FIGS. 4A and 4B depict an example sheath 1 including an annular member 10 and elastic outer layer 50. The annular member 10 has four base members 20 arranged around the circumference of the annular member 10 and four corresponding bridge members 30 extending between opposing pairs of base members 20. In the non-expanded state, the base members 20 and bridge members 30 can define a curvilinear shape in cross-section. For example, as depicted in FIG. 4A, the base members 20 can define two arcuate portions having substantially similar shape terminating in two substantially linear portions extending in a radial direction with respect to the annular member 10. The bridge members 30 can define an S-shape in cross-section.

Similar to the annular member 10 depicted in FIGS. 2A and 3A, in the non-expanded state the annular member 10 of FIG. 4A includes longitudinally extending channels 12, 14 defined between a bridge member 30 and adjacent base member 20 alternating in inward versus outward directionality around the circumference of the annular member 10. The inward and outward extending channels 12, 14 extend radially with respect to the longitudinal axis 11 of the annular member 10. For example, the centerline of each of the inward and outward extending channels 12, 14 creates a 90-degree angle with a line tangent to the diameter of the annular member 10 proximate the opening of the channel.

As described above, the annular member 10 and the elastic outer layer 50 are designed to locally expand in a radial direction between a non-expanded and an expanded state as the prosthetic device 212 is passed through the interior lumen of the sheath 1. FIG. 4B illustrates the annular member 10 and outer layer 50 in an expanded state. The orientation and/or shape of the base members 20 and bridge members 30 of the annular member 10 change during expansion. As illustrated in FIG. 4B, the base members 20 extend and/or elongate in a direction around the circumference of the annular member 10 when transitioned to the expanded state. The bridge members 30 also change in orientation and/or shape during expansion. In the non-expanded state the bridge members 30 extend is a direction toward the longitudinal axis 11/the interior of the annular member 10. Upon expansion of the annular member 10 the bridge members 30 rotate, elongate and/or extend in a direction around the circumference of the annular member 10. For example, the bridge members 30 can flex at joints 32 to facilitate their change in orientation with respect to the base members 20. Upon expansion of the annular member 10, the distance/spacing between adjacent base members 20 increases, widening and changing the shape of the intervening inward and outward extending channels 12, 14 and increasing the overall diameter of the sheath and the outer layer 50.

As illustrated in FIG. 4B, in the expanded state the contact surfaces 22 provided on the base members 20 define the inner diameter of the annular member 10. Likewise, the contact surface 24 defines the outer diameter of the annular member 10, and the corresponding inner diameter of the outer layer 50 in the expanded state. It is contemplated that a portion of the inner surface 16 and outer surface 18 of the base member 20 can also define the inner and outer diameter of the annular member 10 in the expanded state. Contact surfaces 22 reduce the contact surface area between the annular member 10 and the passing device, thereby lowering the coefficient of friction/resistance between the annular member and the passing device.

Figure 5A:
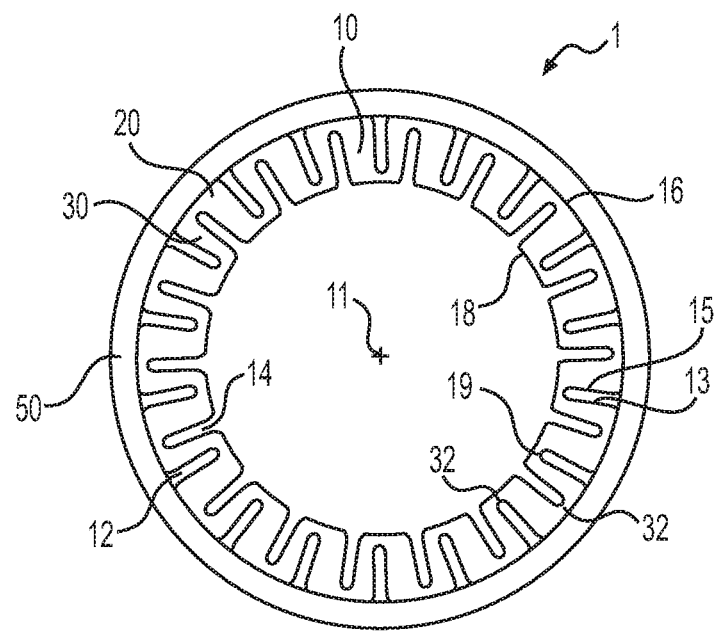
FIG. 5A shows a cross sectional view of an example expandable sheath in the non-expanded state.
Figure 5B:
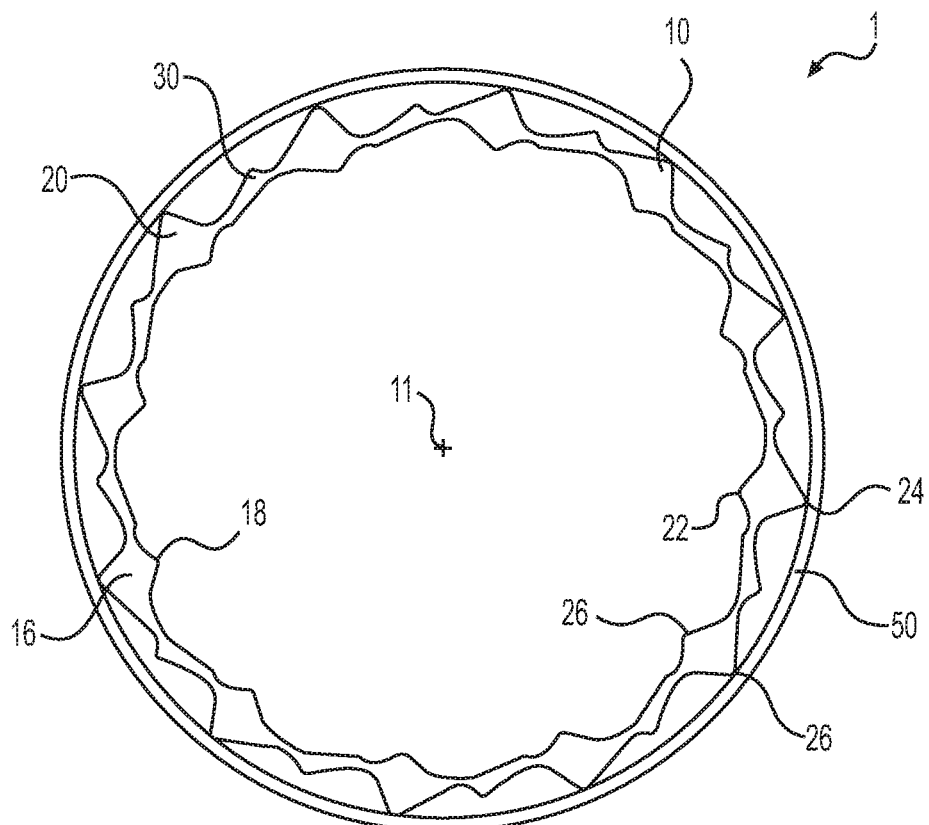
FIG. 5B shows the expandable sheath of FIG. 5A in the expanded state.

FIGS. 5A and 5B depict another example sheath 1 including an annular member 10 and elastic outer layer 50. The annular member 10 has eighteen base members 20 arranged around the circumference of the annular member 10 and eighteen corresponding bridge members 30 extending between opposing pairs of base members 20. In the non-expanded state, the base members 20 and bridge members 30 can define a curvilinear shape in cross-section. For example, as depicted in FIG. 5A, the base members 20 can define a semi-rectangular shape. The bridge members 30 can define an S-shape in cross-section.

Similar to the annular members 10 depicted in FIGS. 2A, 3A and 4A, in the non-expanded state the annular member 10 of FIG. 5A includes longitudinally extending channels 12, 14 defined between a bridge member 30 and adjacent base member 20 alternating in inward versus outward directionality around the circumference of the annular member 10. The inward and outward extending channels 12, 14 extend radially with respect to the longitudinal axis 11 of the annular member 10. For example, the centerline of each of the inward and outward extending channels 12, 14 creates a 90-degree angle with a line tangent to the diameter of the annular member 10 proximate the opening of the channel.

As described above, the annular member 10 and the elastic outer layer 50 are designed to locally expand in a radial direction between a non-expanded and an expanded state as the prosthetic device 212 is passed through the inner lumen of the sheath 1. FIG. 5B illustrates the annular member 10 and outer layer 50 in an expanded state. The orientation and/or shape of the base members 20 and bridge members 30 of the annular member 10 change during expansion. As illustrated in FIG. 5B, the base members 20 extend and/or elongate in a direction around the circumference of the annular member 10 when transitioned to the expanded state. The bridge members 30 also change in orientation and/or shape during expansion. In the non-expanded state the bridge members 30 extend in a direction toward the longitudinal axis 11/the interior of the annular member 10. Upon expansion of the annular member 10 the bridge members 30 rotate, elongate and/or extend in a direction around the circumference of the annular member 10. For example, the bridge members 30 can flex at joints 32 to facilitate their change in orientation with respect to the base members 20. Upon expansion of the annular member 10, the distance/spacing between adjacent base members 20 increases, widening and changing the shape of the intervening inward and outward extending channels 12, 14 and increasing the overall diameter of the annular member 10 and the outer layer 50.

As illustrated in FIG. 5B, in the expanded state the contact surfaces 22 provided on the base members 20 define the inner diameter of the annular member 10. Likewise, the contact surface 24 defines the outer diameter of the annular member 10, and the corresponding inner diameter of the outer layer 50 in the expanded state. Contact surfaces 22 reduce the contact surface area between the annular member 10 and the passing device, thereby lowering the coefficient of friction/resistance between the annular member and the passing device.

Figure 6A:
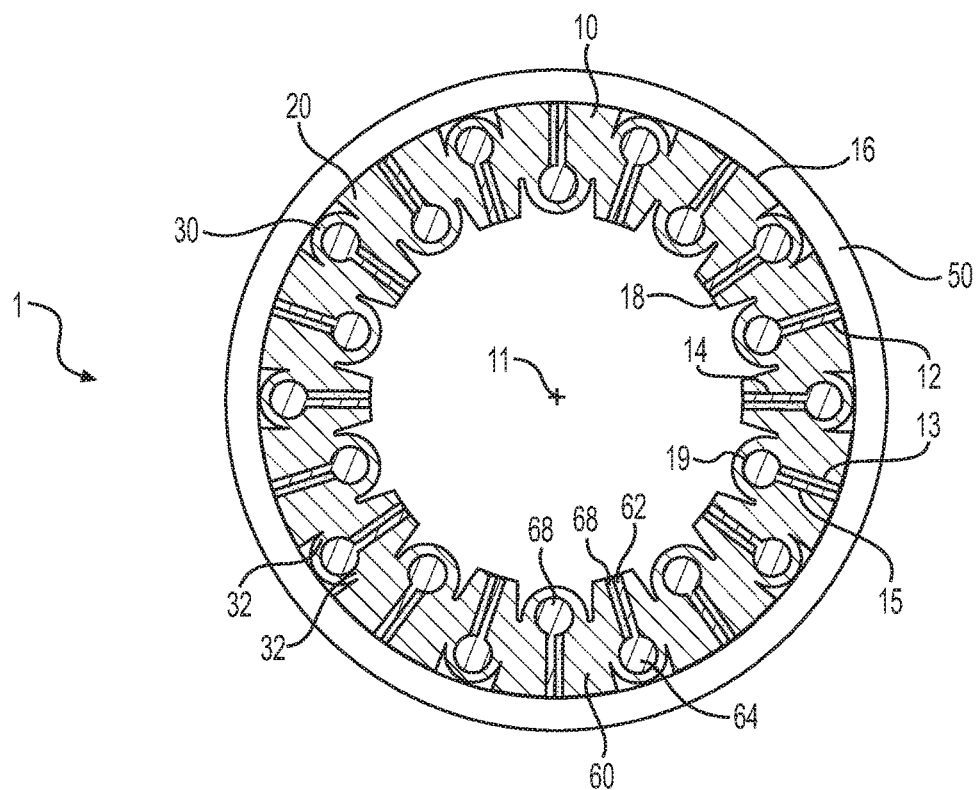
FIG. 6A shows a cross sectional view of an example an expandable sheath in the non-expanded state.
Figure 6B:
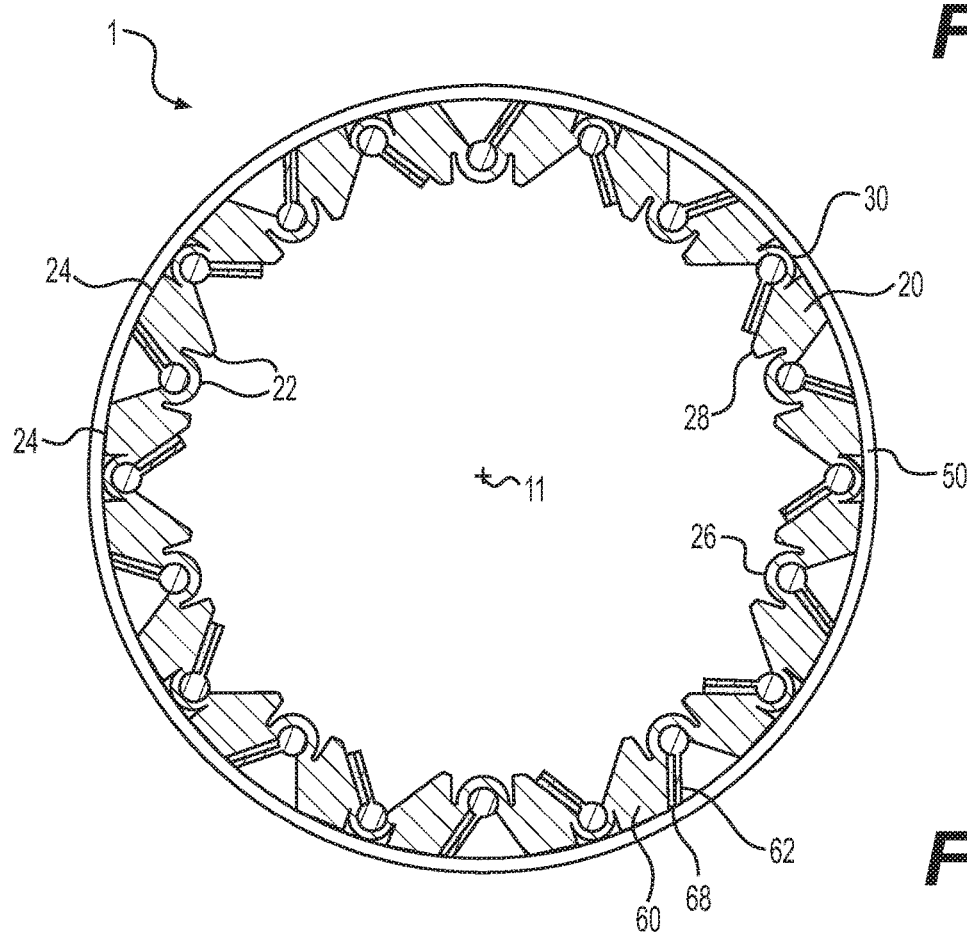
FIG. 6B shows the expandable sheath of FIG. 6A in the expanded state.

FIGS. 6A and 6B depict another example sheath 1 including an annular member 10 and elastic outer layer 50. The annular member 10 has base members 20 arranged around the circumference of the annular member 10 and corresponding bridge members 30 extending between opposing pairs of base members 20.

In the non-expanded state, the base members 20 and bridge members 30 can define a curvilinear shape in cross-section. For example, as depicted in FIG. 6A, the base members 20 define a wedge shape. The bridge members 30 define an arcuate/curved shape in cross-section.

Similar to the annular members 10 depicted in FIGS. 2A, 3A, 4A and 5A, in the non-expanded state the annular member 10 of FIG. 6A includes longitudinally extending channels 12, 14 defined between a bridge member 30 and adjacent base member 20 alternating in inward versus outward directionality around the circumference of the annular member 10. The inward and outward extending channels 12, 14 extend radially with respect to the longitudinal axis 11 of the annular member 10. For example, the centerline of each of the inward and outward extending channels 12, 14 creates a 90-degree angle with a line tangent to the diameter of the annular member 10 proximate the opening of the channel. The shape, in cross-section, of the inward and outward extending channels 12, 14 as depicted in FIG. 6A can include two substantially parallel and straight sides (defined by side wall 13 and side wall 15) that terminate at a rounded end 19. The rounded end 19 can have a width/diameter greater than the width (w) of the corresponding inward and outward extending channels 12, 14.

As described above, the annular member 10 and the elastic outer layer 50 of the sheath 1 are designed to locally expand in a radial direction between a non-expanded and an expanded state as the prosthetic device 112 is passed through the interior lumen of the sheath 1. FIG. 6B illustrates the annular member 10 and outer layer 50 in an expanded state. The orientation and/or shape of the base members 20 and bridge members 30 of the annular member 10 change during expansion. As illustrated in FIG. 6B, the base members 20 rotate, extend and/or elongate in a direction around the circumference of the annular member 10 when transitioned to the expanded state. For example, the base members 20 can rotate with respect to the central axis of each corresponding base member 20. Similarly, the bridge members 30 also change in orientation and/or shape during expansion. In the non-expanded state the bridge members 30 define an arcuate shape that flexes to increase in radius/length upon expansion of the annular member 10. It is also contemplated that the bridge members 30 can rotate, elongate and/or extend in a direction around the circumference of the annular member 10 upon expansion. Upon expansion of the annular member 10, the distance/spacing between adjacent base members 20 increases, widening and changing the shape of the intervening inward and outward extending channels 12, 14 and increasing the overall diameter of the annular member 10 and the outer layer 50. The wall thickness of the annular member 10 is thinner at the bridge members 30 than compared to the base members 20. The decreased thickness at the bridge members 30 eases the bending of the bridge members 30 during expansion, lessening the chance of fracture.

As illustrated in FIG. 6B, in the expanded state the contact surfaces 22 provided on the base members 20 define the inner diameter of the annular member 10. Likewise, the contact surface 24 defines the outer diameter of the annular member 10, and the corresponding inner diameter of the outer layer 50 in the expanded state. Contact surfaces 22 reduce the contact surface area between the annular member 10 and the passing device, thereby lowering the coefficient of friction/resistance between the annular member and the passing device.

As illustrated in FIGS. 2A, 3A, 4A, 5A, 6A and 7A, the size, shape, spacing and number of channels can vary. For example, the non-expanded embodiments of FIG. 2A and FIG. 7B have twenty four combined inward and outward extending channels 12, 14. The non-expanded embodiments of FIG. 3A and FIG. 6A have twenty combined inward and outward extending channels 12, 14, the non-expanded embodiment of FIG. 4A has eight combined inward and outward extending channels 12, 14, and the non-expanded embodiment of FIG. 5A has thirty six combined inward and outward extending channels 12, 14.

Sheaths of the present disclosure can be used with various methods of introducing a prosthetic device into a patient's vasculature. Generally, during use, the expandable sheath 1 is passed through the skin of patient (usually over a guidewire) such that the distal end region of the expandable sheath 1 is inserted into a vessel, such as a femoral artery, and then advanced to a wider vessel, such as the abdominal aorta. The delivery apparatus 210 is then inserted through the expandable sheath 1. The prosthetic device is then delivered to the implantation site and implanted within the patient. During the advance of the prosthetic device through the expandable sheath 1, the device and its delivery system exerts a radially outwardly directed force on the portion of the annular member 10, the annular member 10 exerts a corresponding radially outwardly directed force on the outer layer 50, causing both the annular member 10 and the outer layer 50 to expand locally to accommodate the profile of the device. The expansion of the annular member 10 widens the longitudinally extending channels 12, 14 of the annular member and causes the movement of longitudinally extending contact surfaces 22, 24 toward the inner and outer surfaces 16, 18 of the annular member 10.

As the prosthetic device and its delivery system passes through the expandable sheath 1, the expandable sheath 1 recovers. That is, it returns to its original, non-expanded configuration. In some embodiments, this is facilitated by outer layer 50, which has a higher elastic modulus than annular member 10. The outer layer 50 moves the contact surfaces 22, 24 of the annular member 10 away from the inner and outer surfaces after the passage of the prosthetic valve 212.

As described above, the expandable sheath 1 can be used to deliver, remove, repair, and/or replace a prosthetic device. In one example, the expandable sheath 1 described above can be used to deliver a tissue heart valve to a patient. For example, a tissue heart valve (in a crimped state) can be placed on the distal end portion of an elongated delivery apparatus and inserted into the sheath. Next, the delivery apparatus and crimped heart valve can be advanced through the patient's vasculature to the treatment site, where the valve is implanted.

Beyond transcatheter heart valves, the expandable sheath 1 can be useful for other types of minimally invasive surgery, such as any surgery requiring introduction of an apparatus into a subject's vessel. For example, the expandable sheath 1 can be used to introduce other types of delivery apparatus for placing various types of intraluminal devices (e.g., stents, stented grafts, balloon catheters for angioplasty procedures, etc.) into many types of vascular and non-vascular body lumens (e.g., veins, arteries, esophagus, ducts of the biliary tree, intestine, urethra, fallopian tube, other endocrine or exocrine ducts, etc.).

Figure 7C:
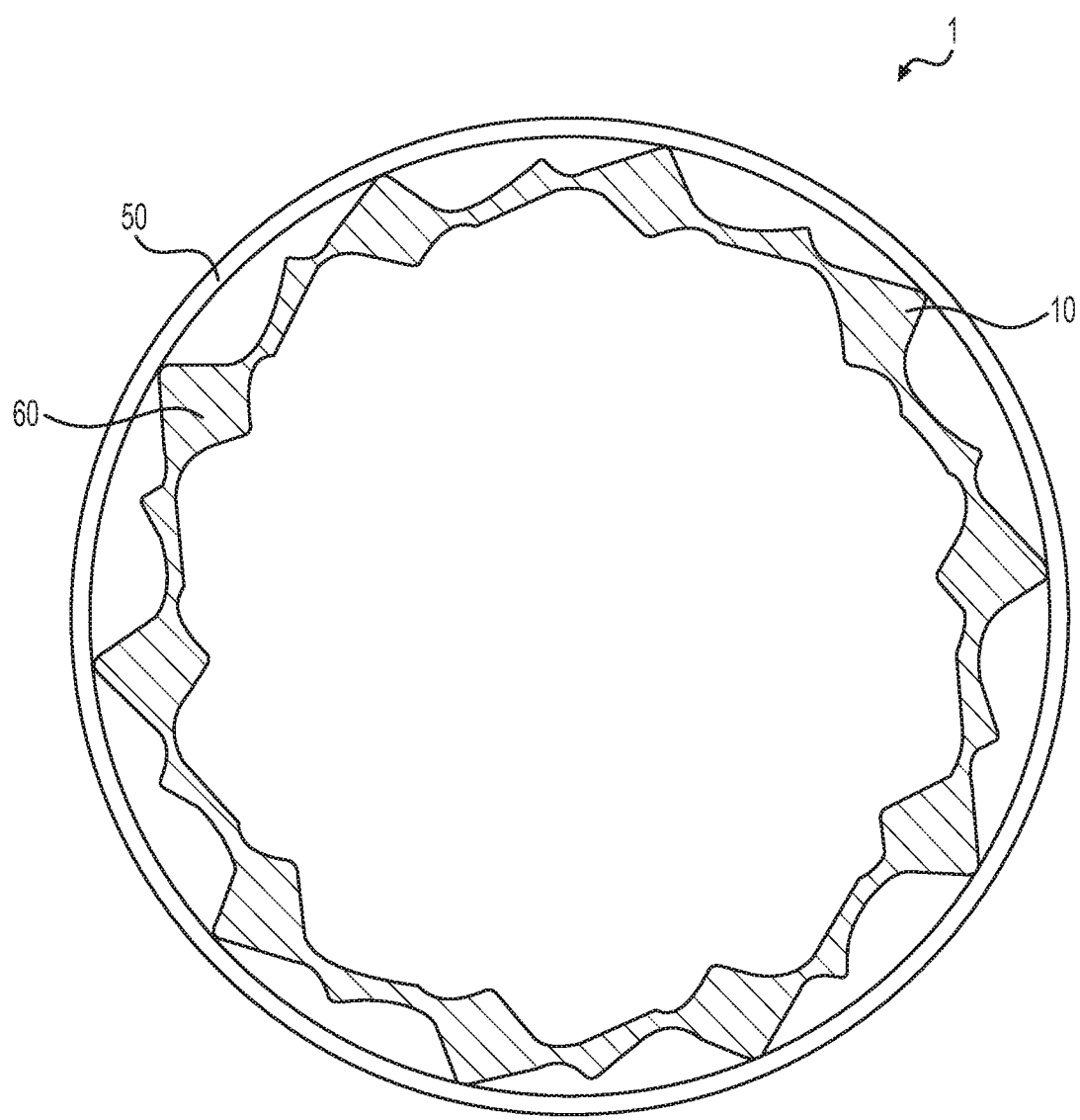
FIG. 7C shows the expandable sheath of FIG. 7B in the expanded state.

FIGS. 7A-7C show cross-sections of an expandable sheath 1 including an annular member 10 and outer layer 50 similar to the annular member 10 and outer layer 50 depicted in FIGS. 2A and 2B. FIG. 7A shows a cross-sections of an expandable sheath 1 during an intermediate processing step that includes a second material in addition to the material used to form the annular member 10. During processing, a tube is coextruded containing a first material 60 and a second material 62. The first material 60 defines the annular member 10 discussed above. The second material 62 does not adhere to the first material 60 and defines a first and second set of longitudinally extending ribbons 64, 66. The second material 62 could be, or could incorporate, nylon, polyethylene terephthalate, and/or polybutylene terephthalate, for example. The first and second set of ribbons 64, 66 form the inward and outward extending channels 12, 14 of the annular member 10 during the extrusion process. The first set of ribbons 64 extends inwardly from the outer surface 16 toward the inner surface 18 of the annular member 10, and the second set of ribbons 66 extends outwardly from the inner surface 18 toward the outer surface 16 of the annular member 10. Each ribbon of a selected set is positioned circumferentially between two ribbons of the other set.

In some embodiments, the second material 62 is a sacrificial material. For example, the ribbons 64, 66 of the second material 62 shown in FIG. 7A are removed after coextrusion, exposing the longitudinally extending channels 12, 14 described above and as shown in the non-expanded embodiment of FIG. 7B.

However, some embodiments, such as the one shown in FIG. 6A, the first material 60 and second material 62 of the annular member 10 is coextruded with a third material 68. This third material 68 is in contact with a portion of the first material 60 and a portion of the second material 62, and adheres to both the first and second materials 60, 62. Because of the adherent third material 68, the second material 62 is not removed. However, it still does not adhere to first material 60. Instead, the third material 68 acts as a tie layer to hold the first and second materials 60, 62 together during expansion of the annular member 10. This eliminates the need to remove the ribbons 64, 66 of the second material 62 prior to use, while still allowing a widening of a channel between the non-adherent first 60 and second 62 materials during the expansion of the annular member 10. The retention of the second material 62 also increases the torque of the finished sheath, so that a user finds it easier to twist the sheath.

Some methods include a step of covering the annular member 10 with the outer layer 50 after coextrusion. As discussed above, the outer layer 50 is formed of, or incorporates, a material with a higher elastic modulus than the annular member 10.

Figure 8:
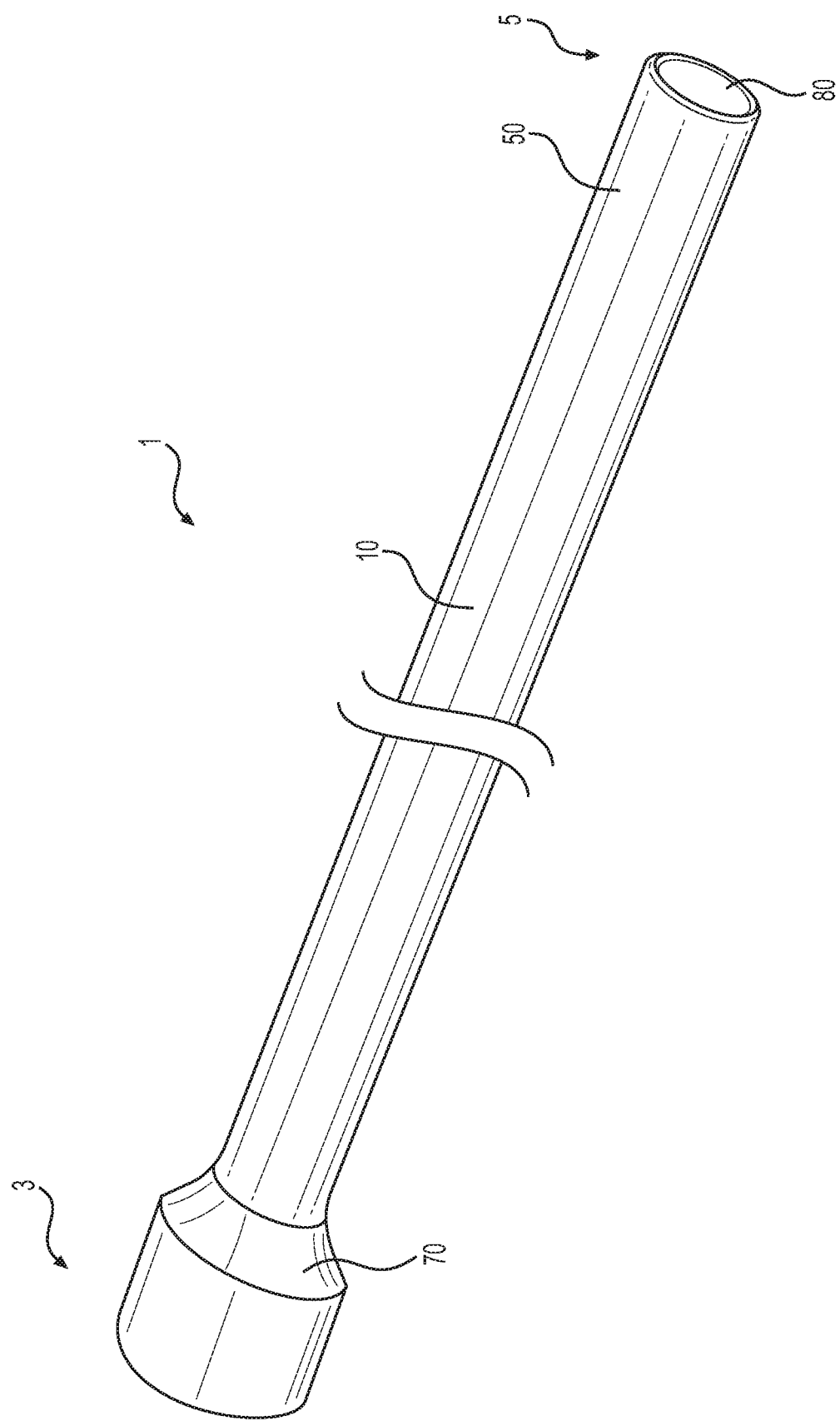
FIG. 8 shows a perspective view of an expandable sheath.

FIG. 8 shows a perspective view of an example sheath 1. In this view, only the outer layer 50 is visible. The sheath 1 comprises a proximal end 3 and distal end 5 opposite the proximal end 3. The sheath 1 can comprise a hemostasis valve inside the lumen of the sheath 1, at or near the proximal end 3. The sheath 1 can include a taper tube 70, a flared proximal end. In some embodiments of the method of making, the taper tube 70 is added to the coextrusion. The addition of the second material 62 will stabilize the coextrusion process and make it possible to add a taper tube 70 during extrusion. This is advantageous because it makes it possible to eliminate the typical taper tube manufacturing steps of flaring (increasing the inner diameter of the sheath) and bonding (increasing the wall thickness after flaring).

Additionally, the sheath 1 can comprise a soft distal tip 80 at the distal end 5. The soft tip 80 can be provided with a lower hardness than the other portions of the sheath 1. In addition to the method of making the expandable sheath described above, a method of making a distal tip 80 of an expandable sheath 1 is demonstrated in the flow chart of FIG. 9. The distal tip 80 can be formed on the annual member 10, outer layer 50, or on the annular member 10 and outer layer 50 combined. The distal tip 80 of the expandable sheath 1 is softer and more elastic than the more proximal regions of the expandable sheath 1 because it must give easily when encountering tissue to reduce the possibility of injury and it must retain the ability to expand after the sealing (reflowing) process wherein the distal tip 80 is sealed to prevent blood from entering the space between the annular member 10 and the outer layer 50. A first step to making the distal tip 80 is to attach a separate distal tube 82 to the distal end 5 of the expandable sheath 1, for example, by reflowing the materials together. Alternatively, the distal tube 82 can be added to the distal end 5 of the sheath 1 via specialized extrusion technology. The distal tube 82 is formed of, or incorporates, a material having greater elasticity than the remainder of the expandable sheath 1. One example material is Pebax.

Next, a portion of the distal tube 82 is pinched to create a longitudinally extending outer crease 84. The pinched portion is folded over an outer surface of the distal tube 82 in a circumferential direction, creating a longitudinally extending flap 86 that is bounded by the outer crease 84 and a longitudinally extending inner crease 85. The inner crease 85 of the flap 86 is cut in a longitudinal direction from the distal edge 83 of the distal tube 82 to a proximally spaced point along the longitudinal axis of the distal tube 82. This creates a longitudinally extending inner edge 87. The flap 86 is cut circumferentially from the outer crease 84 to the inner crease 85 at the proximally spaced point, such that the longitudinal cut of the inner crease 85 meets the circumferential cut at the proximally spaced point. The inner edge 87 of the flap is then extended in a circumferential direction around the outer surface 81 of the distal tube 82 and adhered to the outer surface 81.

Figure 9:
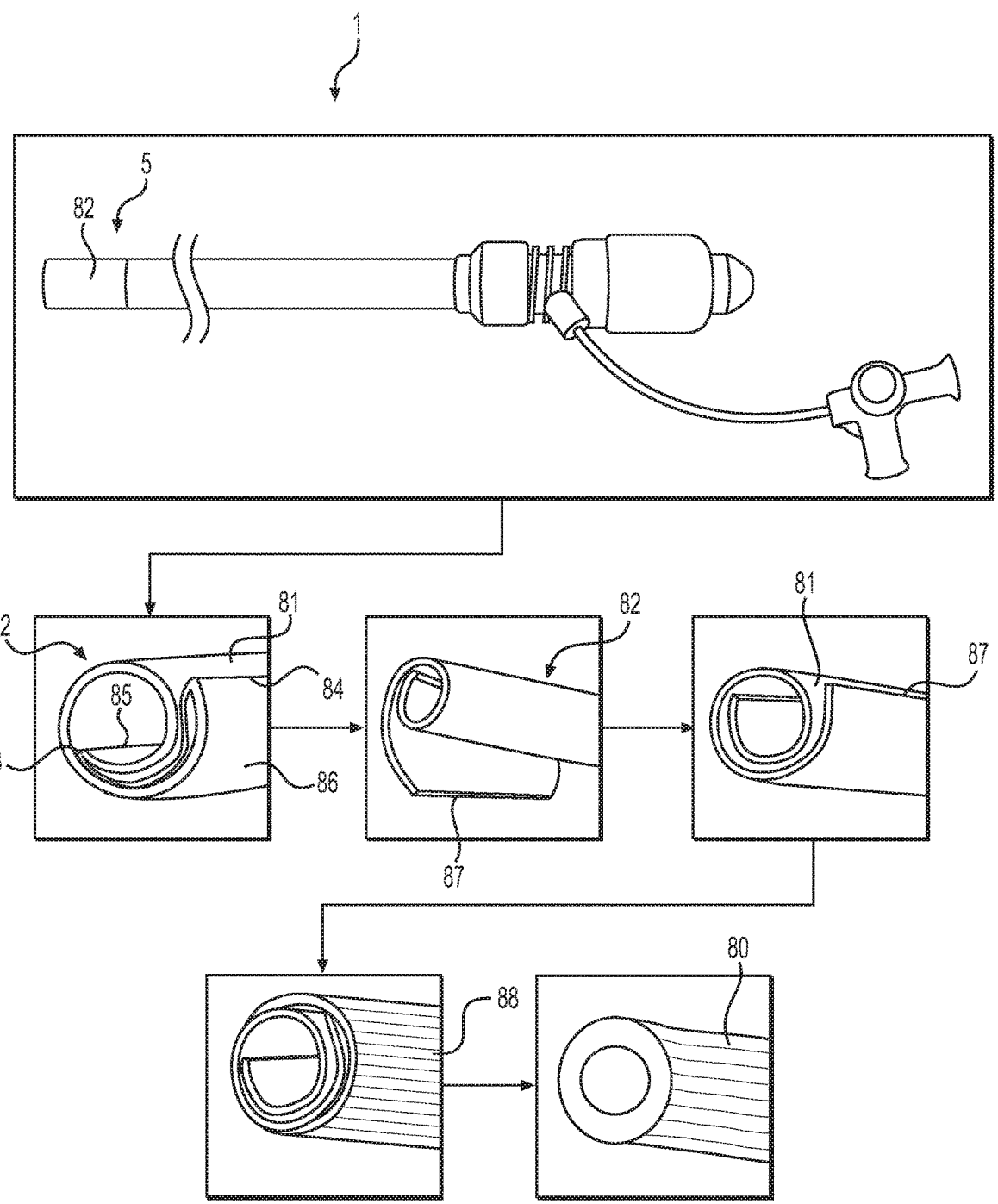
FIG. 9 shows a method of making a distal tip of an expandable sheath.

In some embodiments, such as the one shown in FIG. 9, adhering the inner edge 87 of the flap 86 to the outer surface 81 can include covering the distal end with an outer jacket 88, then reflowing the outer jacket 88 with the distal tube 82 to form a sealed distal end. The outer jacket 88 is also formed of highly elastic materials. One example material is Neusoft. This outer jacket 88 can, in some embodiments, be the same layer as the outer layer 50 shown in FIGS. 2A-B. Because the flap 86 is unfolded and wrapped around the outer surface 81 before reflowing, the final wall thickness of the resulting distal tip varies minimally around its circumference.

Although the foregoing embodiments of the present disclosure have been described in some detail by way of illustration and example for purposes of clarity and understanding, it will be apparent to those skilled in the art that certain changes and modifications may be practiced within the spirit and scope of the present disclosure. It is intended that the scope of the present invention herein disclosed should not be limited by the particular disclosed embodiments described above, but should be determined only by a fair reading of the claims that follow.

What is claimed is:

1. An expandable sheath comprising:
an elongated annular member comprising an inner surface and an outer surface, the annular member further including a bridge member extending between opposing first and second base members spaced around a circumference of the annular member, and
an elastic outer layer extending over the annular member, the elastic outer layer having a lower lubricity than the annular member,
wherein the expandable sheath is radially movable between an expanded state and a non-expanded state,
wherein in the non-expanded state, the annular member includes a first longitudinally extending channel defined between the bridge member and the first base member, the first channel extending inwardly from the outer surface toward a longitudinal axis of annular member, and a second longitudinally extending channel defined between the bridge member and the second base member, the second channel extending outwardly from the inner surface away from the longitudinal axis of the annular member,
wherein in the expanded state, the bridge member extends in a direction around the circumference of the annular member increasing a distance between the first and second base members, and
wherein the elastic layer compresses the expanded annular member toward a non-expanded configuration.

2. The expandable sheath of claim 1, wherein an expanded diameter of the annular member is greater than a non-expanded diameter of the annular member.

3. The expandable sheath of claim 1, wherein an orientation of the first and second base members changes when the annular member moves between the expanded and non-expanded state.

4. The expandable sheath of claim 3, wherein the orientation of the first and second base members rotates about a longitudinal axis of each of the respective base members when the annular member is moved between the expanded and non-expanded state of the annular member.

5. The expandable sheath of claim 1, wherein the first and second base members include a contact edge defining an inner diameter of the annular member in the expanded state.

6. The expandable sheath of claim 1, wherein the bridge member extends in a direction around a circumference of the annular member in the expanded state.

7. The expandable sheath of claim 6, wherein the first and second base members extend in a direction around the circumference of the annular member in the expanded and non-expanded state, wherein at least a portion of the bridge member extends in a direction towards the longitudinal axis of annular member in the non-expanded state and around the circumference of the annular member in the expanded state.

8. The expandable sheath of claim 1, wherein the first and second base members define a rectilinear shape in cross-section.

9. The expandable sheath of claim 1, wherein the bridge member defines an S-shape in cross-section.

10. The expandable sheath of claim 1, wherein the bridge member defines an arcuate shape in cross-section.

11. An expandable sheath comprising:
an elongated annular member radially movable between a non-expanded and expanded state, the annular member including:
base members spaced around a circumference of the annular member,
bridge members extending between opposing pairs of base members, and
an elastic outer layer extending over the annular member, the elastic outer layer having a lower lubricity than the annular member,
wherein in the non-expanded state the annular member includes inwardly and outwardly extending channels extending towards and away from a longitudinal axis of the annular member, respectively, the inwardly and outwardly extending channels defined between each of the opposing pairs of base members and each of the bridge members,
wherein in the expanded state the bridge members extend in a direction around the circumference of the annular member such that a diameter of the annular member is increased and a spacing between opposing pairs of base members is increased from a non-expanded diameter and a non-expanded spacing when the annular member is in the non-expanded state, and
wherein the elastic layer compresses the expanded annular member toward a non-expanded configuration.

12. The expandable sheath of claim 11, wherein one of the inwardly extending channels and one of the outwardly extending channels is provided at opposing ends of a corresponding one of the bridge members.

13. The expandable sheath of claim 11, wherein in the expanded state a depth of each of the inwardly and outwardly extending channels in a radial direction is decreased from a depth of each of the inwardly and outwardly extending channels in the non-expanded state.

14. The expandable sheath of claim 11, wherein the base members include a first, second and third base member and the bridge members include a first and second bridge member,
wherein the first bridge member extends between the first and second base members,
wherein the second bridge member extends between the second and third base members.

* * * * *